United States Patent
Dalessandro et al.

(10) Patent No.: US 6,273,897 B1
(45) Date of Patent: Aug. 14, 2001

(54) SURGICAL BETTRESS AND SURGICAL STAPLING APPARATUS

(75) Inventors: David A. Dalessandro, Fanwood, NJ (US); Murty N. Vyakarnam, New York, NY (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/515,450

(22) Filed: Feb. 29, 2000

(51) Int. Cl.⁷ .......................... A61B 17/10; A61D 17/08
(52) U.S. Cl. .............................. 606/139; 606/219
(58) Field of Search ................................ 606/139, 144, 606/148, 219, 151; 227/176–185

(56) References Cited

U.S. PATENT DOCUMENTS

| | | |
|---|---|---|
| 2,671,444 | 3/1954 | Pease, Jr. . |
| 3,054,406 | 9/1962 | Usher . |
| 3,079,606 | 3/1963 | Bobrov et al. . |
| 3,108,357 | 10/1963 | Liebig . |
| 3,122,140 | 2/1964 | Crowe, Jr. . |
| 3,124,136 | 3/1964 | Usher . |
| 3,272,204 | 9/1966 | Artandi et al. . |
| 3,276,448 | 10/1966 | Kronenthal . |
| 3,284,557 | 11/1966 | Polansky . |
| 3,463,158 | 8/1969 | Schmitt et al. . |
| 3,490,675 | 1/1970 | Green et al. . |
| 3,620,218 | 11/1971 | Schmitt et al. . |
| 3,636,956 | 1/1972 | Schneider . |
| 3,688,317 | 9/1972 | Kurtz . |
| 3,739,773 | 6/1973 | Schmitt et al. . |
| 3,875,937 | 4/1975 | Schmitt et al. . |
| 3,937,223 | 2/1976 | Roth . |
| 4,128,612 | 12/1978 | Roth . |
| 4,132,839 | 1/1979 | Marans et al. . |
| 4,164,046 | 8/1979 | Cooley . |
| 4,186,448 | 2/1980 | Brekke . |
| 4,215,686 | 8/1980 | Gregory et al. . |

(List continued on next page.)

FOREIGN PATENT DOCUMENTS

| | | |
|---|---|---|
| 0334046 | 2/1989 | (EP) . |
| 0325195 | 7/1989 | (EP) . |

OTHER PUBLICATIONS

"Clinical Applications of Bioabsorbable PGA Sheets for Suture Reinforcement and Use as Artificial Pleura"; Tatsuo Nakamura et al.; Japan Lung Surgery Journal 40:10.8(1826)1992.

"Reinforced Staple Line in Severely Empysematous Lungs"; F. M. Juettner, MD et al.; Graz. Austria Journal of Thorac and Cardiovasc Surgery 1989; 97:362–3.

"Median Sternotomy for Bilateral Resecton of Emphysematous Bullae"; Oriane Lima, MD et al.; Ontario, Canada Journal of Thorac and Cardiovasc Surgery 1981; 82:892–897.

"The Current Status of Surgery for Bullous Emphysema", J. E. Connolly, MD et al.; Irvine, California Journal of Thorac and Cardiovasc Surgery 1989; 97:351–61.

"Prevention of Postoperative Pericadial Adhesions by Closure of the Pericardium with Absorbable Polymer Patches"; Malm et al.; The Journal of Thorac and Cardiovascular Surgery, vol. 104, No. 3, pp. 600–607; Sep. 1992.

*Primary Examiner*—Olik Chaudhuri
*Assistant Examiner*—(Vikki) Hoa B. Trinh

(57) ABSTRACT

The present invention provides a surgical stapling apparatus and a buttress, i.e. pledget, for use in the surgical stapling apparatus, which buttress provides sealing for hemostasis and pneumostasis, and which buttress includes a continuous projection, or a plurality of projections, for cooperation with guide channels for thereby attaching the buttress to the staple cartridge or anvil in a releasable pressure fit relationship.

14 Claims, 7 Drawing Sheets

U.S. PATENT DOCUMENTS

| | | |
|---|---|---|
| 4,347,847 | 9/1982 | Usher . |
| 4,354,628 | 10/1982 | Green . |
| 4,397,311 | 8/1983 | Kanshin et al. . |
| 4,429,695 | 2/1984 | Green . |
| 4,452,245 | 6/1984 | Usher . |
| 4,508,253 | 4/1985 | Green . |
| 4,520,817 | 6/1985 | Green . |
| 4,520,821 | 6/1985 | Schmidt et al. . |
| 4,548,202 | 10/1985 | Duncan . |
| 4,568,009 | 2/1986 | Green . |
| 4,608,981 | 9/1986 | Rothfuss et al. . |
| 4,626,253 | 12/1986 | Broadmax, Jr. . |
| 4,633,861 | 1/1987 | Chow et al. . |
| 4,633,873 | 1/1987 | Dumican et al. . |
| 4,633,874 | 1/1987 | Chow et al. . |
| 4,652,264 | 3/1987 | Dumican . |
| 4,655,221 | 4/1987 | Devereux . |
| 4,681,588 | 7/1987 | Ketharanathan . |
| 4,702,917 | 10/1987 | Schindler . |
| 4,728,020 | 3/1988 | Green et al. . |
| 4,784,137 | 11/1988 | Kulik et al. . |
| 4,832,686 | 5/1989 | Anderson . |
| 4,838,884 | 6/1989 | Dumican et al. . |
| 4,840,626 | 6/1989 | Linsky et al. . |
| 4,865,031 | 9/1989 | O'Keeffe . |
| 4,892,244 | 1/1990 | Fox et al. . |
| 4,905,692 | 3/1990 | More . |
| 4,930,574 | 6/1990 | Barak . |
| 4,932,960 | 6/1990 | Green et al. . |
| 4,955,959 | 9/1990 | Tompkins et al. . |
| 4,960,866 | 10/1990 | Bendix et al. . |
| 4,983,745 | 1/1991 | Muller et al. . |
| 5,002,551 | 3/1991 | Linsky et al. . |
| 5,011,493 | 4/1991 | Belykh et al. . |
| 5,014,899 | 5/1991 | Presty et al. . |
| 5,040,715 | 8/1991 | Green et al. . |
| 5,042,707 | 8/1991 | Taheri . |
| 5,061,281 | 10/1991 | Mares et al. . |
| 5,066,772 | 11/1991 | Tang et al. . |
| 5,079,075 | 1/1992 | Yanasaki et al. . |
| 5,102,983 | 4/1992 | Kennedy . |
| 5,141,144 | 8/1992 | Foslien et al. . |
| 5,156,614 | 10/1992 | Green et al. . |
| 5,156,797 | 10/1992 | Yamasaki et al. . |
| 5,176,692 | 1/1993 | Wilk et al. . |
| 5,203,864 | 4/1993 | Phillips . |
| 5,263,629 | 11/1993 | Trumbull et al. . |
| 5,346,115 | 9/1994 | Perouse et al. . |
| 5,397,324 | 3/1995 | Caroll et al. . |
| 5,433,721 | 7/1995 | Hooven et al. . |
| 5,441,193 | 8/1995 | Gravener . |
| 5,503,638 | 4/1996 | Cooper et al. . |
| 5,542,594 | 8/1996 | McKean et al. . |
| 5,702,409 | 12/1997 | Rayburn et al. . |
| 5,752,965 | 5/1998 | Francis et al. . |
| 5,766,188 | 6/1998 | Igaki . |
| 5,814,057 | 9/1998 | Oi et al. . |
| 5,833,695 * | 11/1998 | Yoon ................................ 606/139 |
| 5,964,774 | 10/1999 | McKean et al. . |

\* cited by examiner

ID: 6,273,897 B1

SURGICAL BETTRESS AND SURGICAL STAPLING APPARATUS

FIELD OF THE INVENTION

This invention relates to a surgical buttress that eliminates or minimizes loss or leakage of bodily fluids, including blood or air, and a surgical stapling apparatus that applies the buttress to body tissue.

BACKGROUND OF THE INVENTION

During surgical procedures it is necessary to approximate organ tissue with surgical staples. Surgeons often use linear cutter stapling devices to suture body organs and tissues such as lung, esophagus, stomach, duodenum and other body organs. Such devices apply a plurality of laterally spaced rows of staples on opposite sides of a tissue cut.

Examples of such surgical staplers are disclosed in U.S. Pat. Nos. 4,633,861 and 4,892,244, the disclosures of which are incorporated herein by reference. The surgical stapler includes a pair of cooperating elongated jaw members. One of the jaws members includes a staple cartridge with at least two laterally spaced rows of staples and the other jaw member includes an anvil with staple closing depressions in alignment with the rows of staples in the cartridge. A pusher block is directed longitudinally along the jaws to sequentially eject staples from the cartridges in a manner that closes the staples against the anvil to form laterally spaced lines of staples through tissues that is gripped between the jaws. A knife is associated with the pusher block so as to move forward along the jaws to cut the tissue along the line between the previously formed staple rows.

When operating on tissue it is desirable to close open blood vessels (hemostasis) along the cut line. And in procedures that involve approximating lung tissue it is necessary to seal the lung to avoid air leakage (pneumostasis). U.S. Pat. No. 5,263,629 discloses a method and apparatus for achieving hemostasis along a staple line by utilizing a pledget material positioned adjacent to at least one surface of the tissue. The line of staples is formed so as to extend through the tissue and the absorbable pledget material. The pledget material is selected so as to substantially uniformly distribute pressure along the staple line and thereby cause substantial hemostasis along the tissue cut. Preferred materials for these pledgets are sterile absorbable tightly woven fabrics. The pledgets may be secured to the stapler by spaced apart ultrasonic welds or spaced apart adhesive bonds.

U.S. Pat. No. 5,964,774, the contents of which is hereby incorporated by reference in its entirety, also discloses surgical stapling apparatus having tissue bolstering material disposed thereon for application of the material and staples to body tissue. Releasable attachment of the tissue bolstering material to the stapling device is accomplished via a plurality of pins or a combination of pins and clips.

It would be advantageous to provide a bolstering material that is releasably attachable to the staple cartridge and/or the anvil of a surgical stapling apparatus without conventional pins, clips, welds or adhesives.

SUMMARY OF THE INVENTION

The present invention provides a surgical buttress, i.e. pledget, for approximating body tissue, which buttress provides sealing for hemostasis and pneumostasis, and which buttress comprises a continuous projection, or a plurality of projections, wherein the projection(s) are of sufficient number, dimension and spatial relationship effective to provide a releasable pressure fit of the projection into means for receiving the projections located in the staple cartridge or the anvil of a surgical stapling apparatus when placed in cooperation therewith, thereby maintaining the buttress in covering relationship with the cartridge and/or anvil. The invention also provides a surgical stapling apparatus comprising the improved buttress.

BRIEF DESCRIPTION OF THE DRAWINGS

FIG. 13b is a side elevational view of Fig.13a;

FIG. 14b is a side elevational view of FIG. 14a;

DETAILED DESCRIPTION OF THE INVENTION

Figure 1:
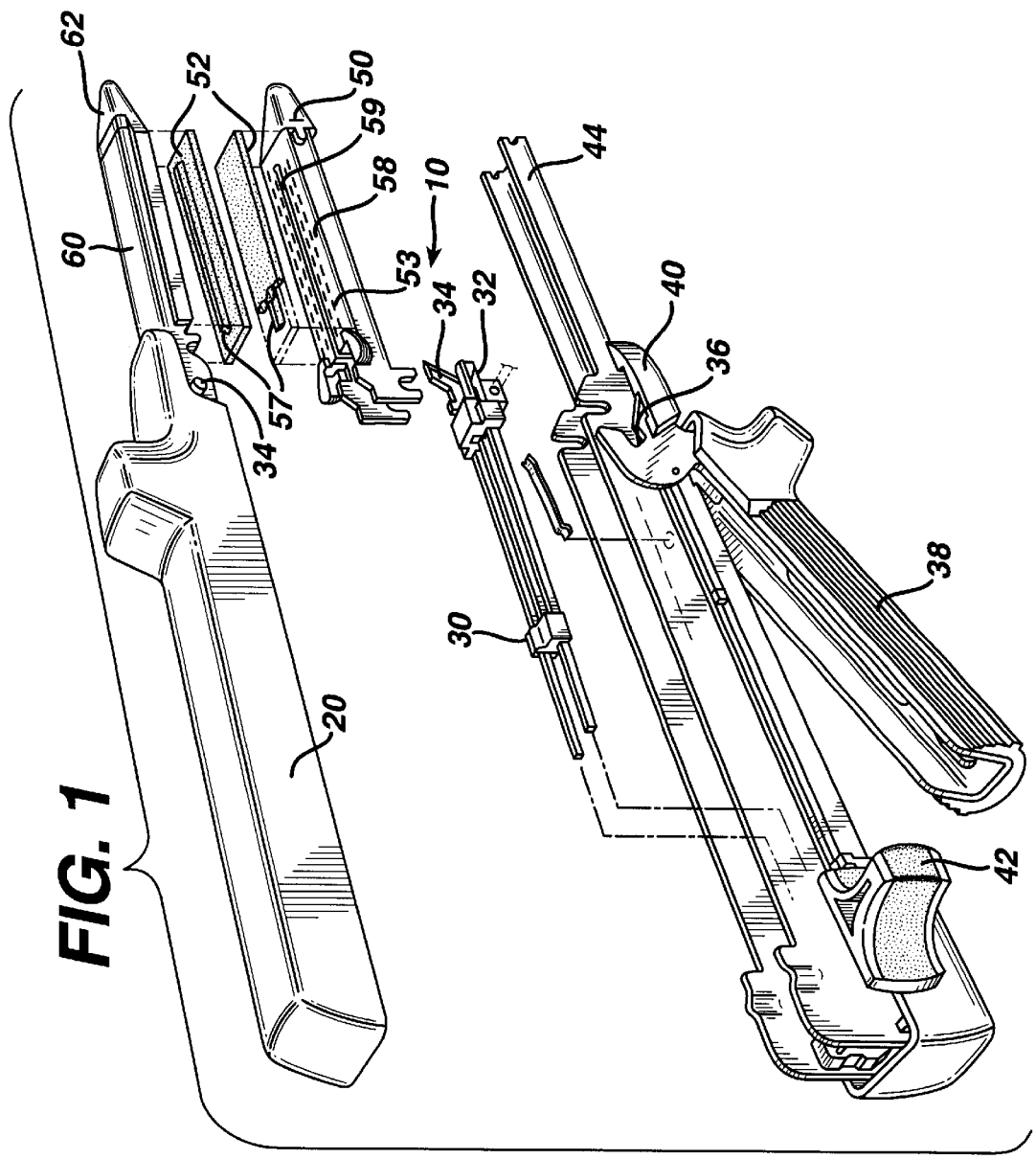
FIG. 1 is an exploded view in perspective of a non-endoscopic surgical stapler apparatus of the present invention.

Referring to FIG. 1, there is shown a typical non-endoscopic surgical stapler 10 generally of the type disclosed in U.S. Pat. Nos. 4,633,861, 4,892,244, and 5,263,629, the disclosure of which patents are incorporated herein by reference in their entirety for a more complete discussion of certain structural details of the apparatus. Surgical stapler 10 includes an upper jaw 20, a firing means 30, a lower jaw 40 and a staple cartridge 50 that is received within the lower jaw 40.

The firing means 30 includes a pusher block and firing wedge assembly 32 and a knife 34 located therebetween. The firing wedges are directed through longitudinal slots, or knife guide channels 59, located in staple cartridge 50. Cartridge 50 is releasably received within a lower jaw channel 44. A firing knob 42 activates the firing means 30 to move the firing wedges 32 through the staple cartridge 50. As the firing wedges 32 pass longitudinally through the knife guide channels of the cartridge, they contact staple drivers (not shown), which in turn eject the staples (not shown) through openings 53 in the staple cartridge 50.

Figure 2:
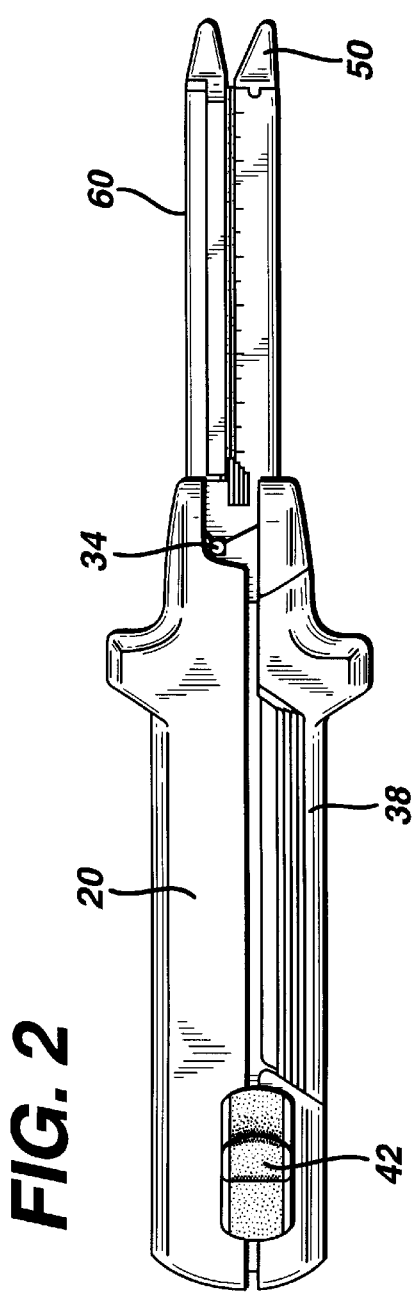
FIG. 2 is a side elevational view of the stapler apparatus shown in FIG. 1 with its jaws in a clamping position.

Upper jaw 20 is pivotally connected to lower jaw 40 through a latch pin that is received in a slot 36 associated with a latch member 38 to latch the jaw members together at an intermediate position along the length thereof. Movement of latch member 38 between its latched position, as shown in FIG. 2, and its unlatched position, as shown in FIG. 1, causes the jaws 20 and 40 to move toward and away from each other.

Figure 3:
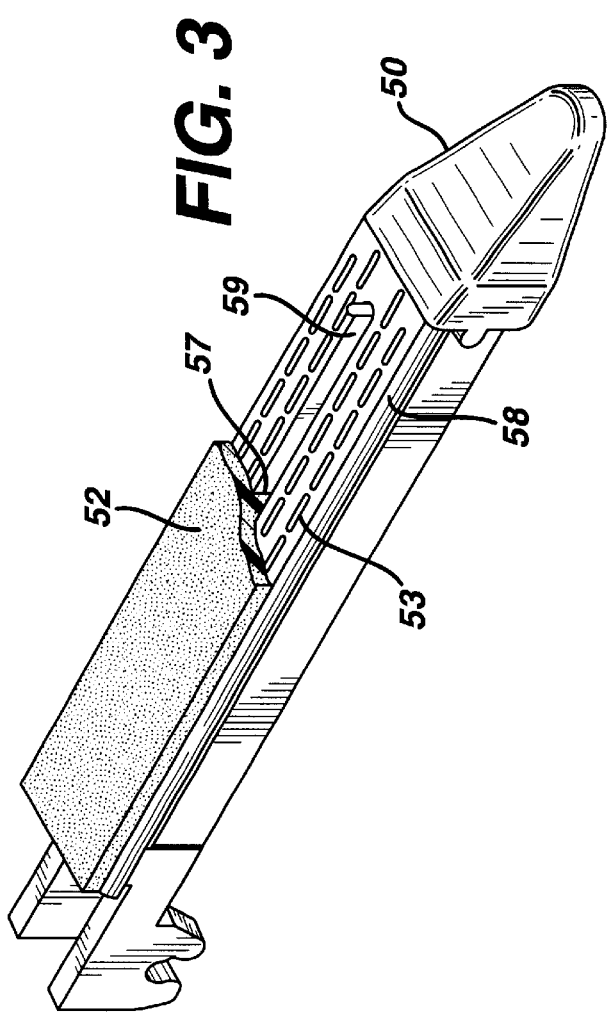
FIG. 3 is a perspective view of a staple cartridge that includes a buttress in accordance with the invention.

Referring to FIGS. 1 and 3 there is shown one embodiment of a disposable staple cartridge 50 containing a plurality of surgical staples (not shown) of the type generally disclosed in U.S. Pat. Nos. 4,633,861, 4,982,244, and 5,263,629. Cartridge 50 preferably is provided with two pairs of spaced-apart parallel lines of staples. Cartridge 50 includes a buttress 52 releasably attached thereto in covering relationship with an upper surface 58 having openings 53 through which the staples are ejected.

While staple cartridge 60 may have a conventional buttress releasably attached thereto by conventional means in embodiments of the present invention where buttress 52 is attached to anvil 60 according to the present invention, the buttress according to the present invention may be releasably attached to the cartridge by inserting the projection(s) of the buttress into the knife guide channels of the cartridge, thereby providing a releasable pressure fit of the buttress in the cartridge. By releasable pressure fit, it is meant that the projection(s) of the buttress, when inserted into the knife guide channel, cooperate with the channels so as to create minimum pressure sufficient to maintain the position of the buttress relative to the cartridge or anvil in a covering relationship during normal use of the stapling apparatus, and maximum pressure sufficient to provide release of the buttress from the cartridge or anvil as the knife blade progresses through the channels upon firing of the stapling apparatus.

As seen in FIG. 3, buttress 52 is attached to staple cartridge 50 in a releasable pressure fit relationship by placing projection 57 into knife guide channel 59. The continuous projection, or alternately a plurality of projections, is located longitudinally along the mid-portion of buttress 52, such that once the projection(s) is placed in cooperation with knife guide channel 59 by insertion therein, the buttress maintains its covering relationship with upper surface 58 of cartridge 50. The projection(s) must be of sufficient number, dimension and spacial relationship to provide a releasable pressure fit with knife guide channel 59.

Referring to FIGS. 1 and 7–10, the front portion of upper jaw 20 includes an anvil 60 that includes longitudinal rows of uniformly spaced staple-forming pockets 63. A disposable anvil tip 62 is releasably mounted at the front end of anvil 60 and is received rearwardly thereinto. Anvil tip 62 includes a leading tapered portion 64 to facilitate the insertion of the jaw member into hollow, tubular body organs or small openings in tissue sections. Anvil tip 62 includes a pair of spaced apart elongated inner side walls 66 that extend into anvil 60 and a pair of spaced apart elongated outer side walls 68 that extend alongside anvil 60. Buttress 52 is releasably attached to anvil 60 by attachment means 67.

In accordance with preferred embodiments of the invention, buttress 52 is releasably attached to anvil 60 by a continuous projection, or a plurality of projections 57 releasably pressed into anvil knife guide channel 69. The projection(s) 67 is located longitudinally along the mid-portion of the buttress 52 such that once projection(s) 67 is placed in cooperation with knife guide channel 69 by insertion therein, the buttress maintains its covering relationship with anvil 60. The projection(s) must be of sufficient number, dimension and spacial relationship to provide a releasable pressure fit with knife guide channel 69. Additional conventional means for attaching buttress 52 to anvil 60 therefore is not required.

In preferred embodiments where the buttress is made from a compressible material, the width of the projection may be greater than the width of the knife guide channel. Compression of the buttress material upon insertion into the channel creates the pressure within the channel that is required to maintain the covering relationship of the buttress relative to the cartridge or anvil surface. Actual dimensions and number of the projection(s) is dependent upon the dimension of the channel and the material used to prepare the buttress.

Employing a plurality of projections or tabs in the buttress can advantageously effect a releasable pressure fit. The projections may be either continuous or intermittently spaced along the length of the buttress to coincide with the channels that guide the knife blade of the stapling apparatus when the buttress is placed in cooperation with the cartridge or the anvil. The precise number and location of the projections is not so critical so long as a releasable pressure fit is achieved and the knife can pass effectively through the guide channel, thereby providing release of the buttress from the stapler. In addition, tissue is often manipulated within the jaws of the stapling apparatus prior to actuation. This manipulation applies lateral forces to the cartridge and anvil of the stapling apparatus. The lateral forces may be high enough to dislodge a releasably attached buttress. The releasable pressure fit of the buttress to the staple cartridge or anvil in accordance with the present invention also provides lateral stability of the buttress during delivery.

Figure 12:
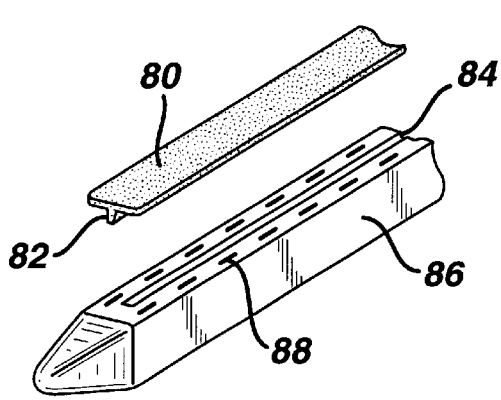
FIG. 12 is a side elevational view of a buttress and anvil according to the present invention.
Figure 13A:
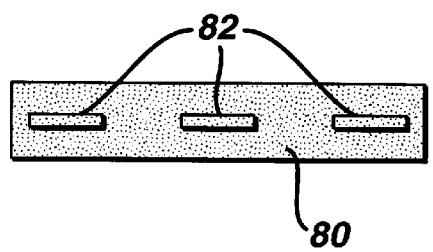
FIG. 13a is a top plan view of a buttress containing a plurality of projections.
Figure 13B:
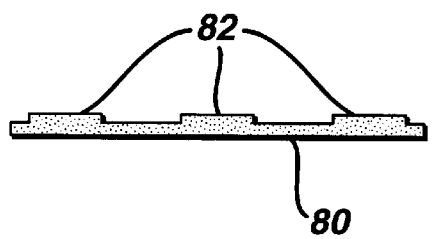
Figure 15:
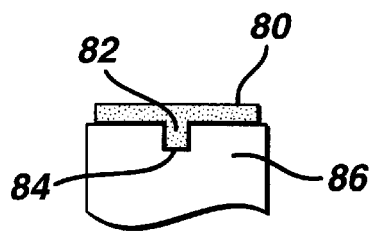
FIG. 15 is a cross-sectional view of a buttress and anvil.
Figure 14A:
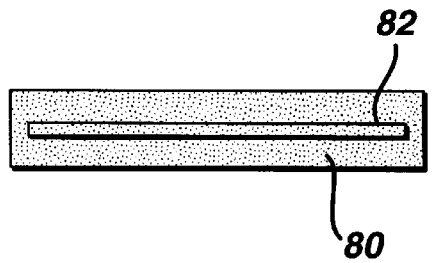
FIG. 14a is a top plan view of a buttress comprising a continuous projection.
Figure 16:
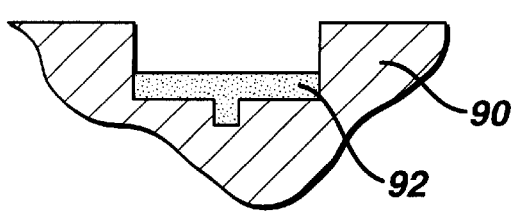
FIG. 16 is a cross-sectional view of a mold containing foam material used to prepare a buttress according to the invention.
Figure 14B:
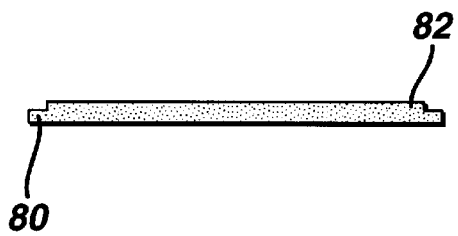

Referring to FIGS. 12–14a, preferred foam buttresses according to the present invention are disclosed. In FIG. 12, buttress 80 comprising projection 82 is shown in relationship to anvil 86. Anvil 86 comprises knife guide channel 84 for receiving projection 82 and pockets 88 for receiving staples. In FIGS. 13a and 13b, buttress 80 comprises a plurality of projections 82 located longitudinally along the mid-portion of the buttress. In FIGS. 14a and 14b, buttress 80 comprises a continuous projection located longitudinally along the mid-portion of the buttress. FIG. 15 exemplifies a buttress 80 in combination with anvil 86, wherein projection 82 is in cooperation with knife guide channel 84. While FIGS. 12 and 15 exemplify embodiments where the buttress is attached to the stapler anvil, the buttress can be attached to the staple cartridge in like manner. FIG. 16 shows mold 90 containing liquid foam material 92. The liquid foam 92 is lyophilized to prepare the foam buttress of the present invention.

Figure 17:
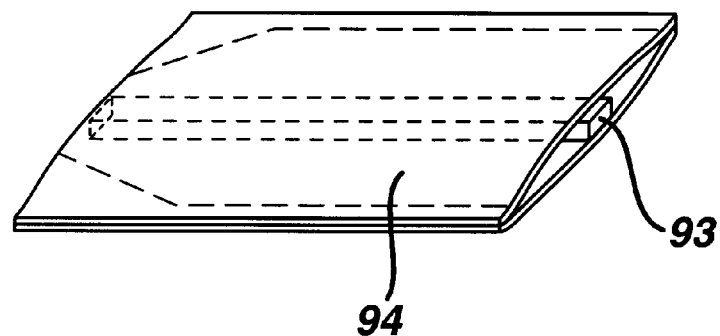
FIG. 17 is a perspective view of a buttress according to the present invention.
Figure 18:
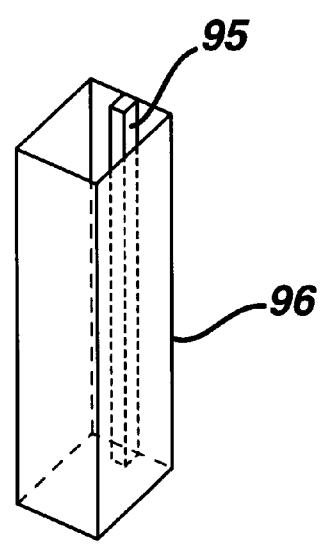
FIG. 18 is a perspective view of a buttress according to the present invention.
Figure 19:
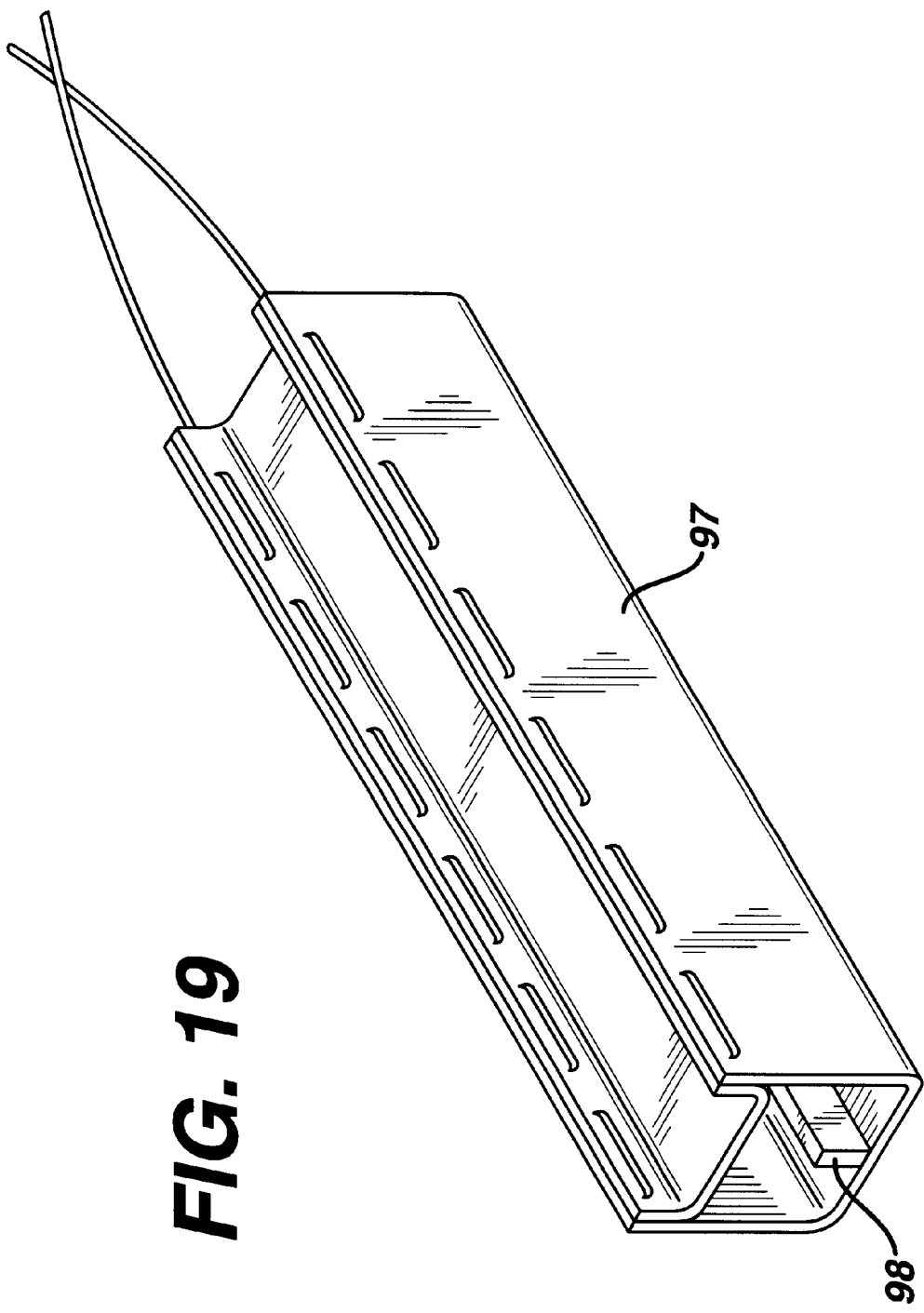
FIG. 19 is a perspective view of a buttress according to the present invention.

FIGS. 17 and 18 show buttresses 94 and 96, respectively, of the type disclosed in U.S. Pat. No. 5,814,057, hereby incorporated by reference in its entirety, each modified to include projection 93 and 95, respectively. FIG. 19 shows buttress 97 of the type disclosed in U.S. Pat. No. 5,503,638, hereby incorporated by reference in its entirety, modified to include projection 98.

While preferred embodiments utilize the knife guide channel of the cartridge and/or anvil as the means for receiving the projection(s) in a releasable pressure fit relationship, other means for receiving the projection(s) may be utilized. For example, the projections may be configured to cooperate with the openings in the staple cartridge through which the staples are ejected, or the openings in the anvil for receiving the staples. In addition, the cartridge and/or anvil may be modified or designed to include openings or channels for cooperation with the projection(s) other than the staple openings or knife guide channel. For example, longitudinal channels may be located parallel to and offset from the knife guide channels located in the mid-portion of the cartridge and/or anvil. Other openings also may be included in the cartridge and/or anvil in spaced-apart relationship so as to cooperate with corresponding buttress projection(s), thereby providing the releasable pressure fit.

In accordance with preferred embodiments of the invention, the buttress preferably is made from a compliant, bioabsorbable foam material. The foam material uniformly distributes pressure along the staple line to cause substantial hemostasis or pneumostasis along the tissue cut. The foam material also provides a medium for the staples to hold onto in the case of thin or diseased tissue. The material also absorbs impact and reduces trauma. The compressible nature of bioabsorbable foam materials allows for the projections to be slightly wider than the knife guide channels in either the staple cartridge or the anvil. The compressible foam material uniformly distributes the pressure along the channel guide to effect a releasable pressure fit of the projection within the guide channel.

Suitable foams for use in the present invention are prepared from biocompatible elastomeric polymers. Preferably this polymer also will be bioabsorbable. Examples of suitable bioabsorbable elastomers are described in U.S. Pat. No. 5,468,253, hereby incorporated by reference in its entirety. Preferably the bioabsorbable biocompatible elastomers are based on aliphatic polyester, including but not limited to those selected from the group consisting of elastomeric copolymers of $\epsilon$-caprolactone and glycolide (preferably having a mole ratio of $\epsilon$-caprolactone to glycolide of from about 35:65 to about 65:35, more preferably 45:55 to 35:65); elastomeric copolymers of $\epsilon$-caprolactone and lactide (including L-lactide, D-lactide, blends thereof or lactic acid copolymers (preferably having a mole ratio of $\epsilon$-caprolactone to lactide of from about 35:65 to about 65:35 and more preferably 45:55 to 30:70, or from about 95:5 to about 85:15)); elastomeric copolymers of p-dioxanone (1,4-dioxan-2-one) and lactide (including L-lactide, D-lactide and lactic acid (preferably having a mole ratio of p-dioxanone to lactide of from about 40:60 to about 60:40); elastomeric copolymers of $\epsilon$-caprolactone and p-dioxanone (preferably having a mole ratio of $\epsilon$-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide (including L-lactide and D-lactide) and lactic acid copolymers (preferably having a mole ratio of trimethylene carbonate to lactide of from about 30:70 to about 70:30). These elastomeric polymers will have an inherent viscosity of from about 1.2 dL/g to about 4 dL/g, preferably an inherent viscosity of from about 1.2 dL/g to about 2 dL/g and most preferably an inherent viscosity of from about 1.4 dL/g to about 2 dL/g as determined at 25° C. in a 0.1 gram per deciliter (g/dL) solution of polymer in hexafluoroisopropanol (HFIP).

Preferably, the elastomers will exhibit a high percent elongation and a low modulus, while possessing good tensile strength and good recovery characteristics. In the preferred embodiments of this invention, the elastomer from which the foams are formed will exhibit a percent elongation greater than about 200 preferably greater than about 500. It will also exhibit a modulus (Young's Modulus) of less than about 4000 psi, preferably less than about 20,000 psi. There properties, which measure the degree of elasticity of the bioabsorbable elastomer, are achieved while maintaining a tensile strength greater than about 500 psi, preferably greater than about 1,000 psi, and a tear strength of greater than about 50 lbs/inch, preferably greater than about 80 lbs/inch.

These elastomer polymers may be foamed by lyophilization, supercritical solvent foaming (i.e., as described in EP 464,163B1), gas injection extrusion, gas injection molding or casting with an extractable material (i.e., salts, sugar or any other means known to those skilled in the art). Currently it is preferred to prepare bioabsorbable, biocompatible elastomers by lyophilization. One suitable method for lyophilizing elastomeric polymers to form foam buttresses according to the present invention is described in the Example. Pharmaceutically active compounds may be incorporated into the foam buttress to further treat the patient, including but not limited to antibiotics, antifungal agents, hemostatic agents, anti-inflammatory agents, growth factors and the like.

The aliphatic poly(ester)s generally are prepared by a ring opening polymerization of the desired proportions of one or more lactone monomers in the presence of an organometallic catalyst and an initiator at elevated temperatures. The organometallic catalyst preferably is a tin-based catalyst, e.g. stannous octoate, and is present in the monomer mixture at a molar ratio of monomer to catalyst ranging from about 15,000/1 to about 80,000/1. The initiator typically is an alkanol (such as 1-dodecanol), a polyol (such as 1,2-propanediol, 1,3-propanediol, diethylene glycol, or glycerol, poly(ethylene glycol)s, poly(propylene glycol)s and poly (ethylene-co-propylene glycol)s), a hydroxyacid, or an amine, and is present in the monomer mixture at a molar ratio of monomer to initiator ranging from about 100/1 to about 5000/1. The polymerization typically is carried out at a temperature range from about 80 to about 220° C., preferably 160 to 190° C., until the desired molecular weight and viscosity are achieved.

In certain embodiments, the projections(s) may comprise materials different from the buttress itself, depending on the particular properties required for the particular application. For example, the projection(s) may be made more or less flexible or compressible from the buttress by selecting certain monomers at selected ratios effective to provide polymers which in turn provide the desired properties to the projection(s) and buttress, respectively.

Other materials used in preparing buttresses according to the invention include polytetraflouroethylene and non-woven materials as described in U.S. Pat. Nos. 5,814,057 and 5,503,638. Buttresses made from PTFE and comprising projection(s) according to the present invention may be prepared by placing a bead of PTFE along the length of the buttress prior to formation thereof and then sintering to form the buttress comprising the projection. For non-woven materials, the projection(s) may be molded or pressed into the buttress. In addition, the buttress may be gathered and stitched to form a projection in the non-woven buttress. Additionally, the projection(s) may be formed by chemically bonding or sintering of a bead of material along the surface of the buttress to the buttress.

The method for achieving hemostasis along a tissue cut having open blood vessels in accordance with the invention will now be discussed along with a discussion of the operation of stapling apparatus 10. The tissue or walls of organ sections to be stapled and cut are positioned and clamped between upper jaw 20 and lower jaw 40 and latch 38 is in its latched position as shown in FIG. 2. At least one, and preferably both, of the cartridge 50 and the anvil 60 are provided with buttress 52 as discussed above.

Figure 4:
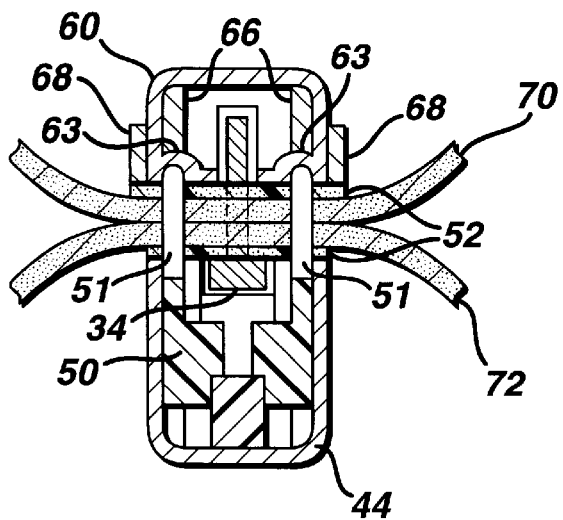
FIG. 4 is a sectional view taken through the jaws of the surgical stapler showing a staple being formed through adjacent tissue sections and buttress positioned adjacent to the outer surface of each of the tissue sections.

After the tissue segments are clamped between the jaw members, stapler 10 is fired by advancing firing knob 42 to activate the pusher block and knife blade assembly 30. The firing wedges 32 advance distally through the staple cartridge 50 into engagement with staple drivers to sequentially drive staples 51 through the openings 53 in two pairs of spaced apart parallel lines of staples. The staples 51 contact a corresponding staple forming pocket associated with anvil 60 to form generally a B-shaped configuration or a flat configuration staple. Referring to FIG. 4, the formed staples extend through the tissue sections 70 and 72 and buttress 52. At the same time, knife blade 34 is distally advanced through a longitudinal slot, i.e. knife guide channel, formed in anvil 60 and staple cartridge 50 to cut the tissue sections gripped between the jaw sections between the two pairs of spaced apart parallel lines of staples.

After the firing wedges 32 are fully advanced to form all of the staples in cartridge 50, the pusher block and knife blade assembly 30 is returned to its start position by retraction of firing knob 42. The latch member 38 may then be moved to its unlatched position, separating jaws 20 and 40, so as to permit the device 10 to be unclamped and removed from the tissue sections releasing the foam buttress strips from the anvil tip 62 and/or cartridge 50.

Figure 5:
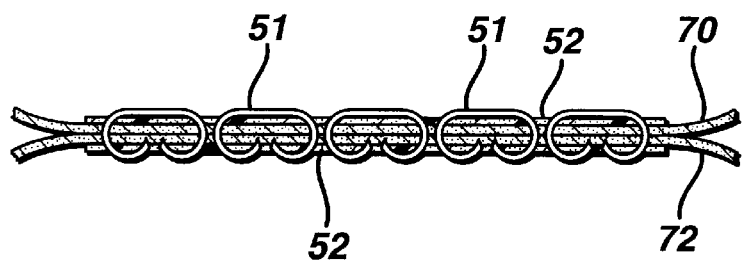
FIG. 5 is a longitudinal sectional view showing adjacent tissue sections joined together by staples and buttress in accordance with the invention.
Figure 6:
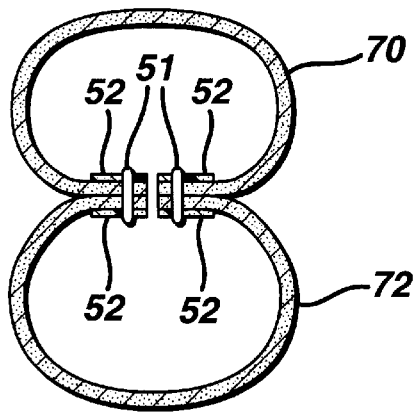
FIG. 6 is a transverse sectional view showing adjacent organ segments joined together by staples and buttress in accordance with the invention.
Figure 7:
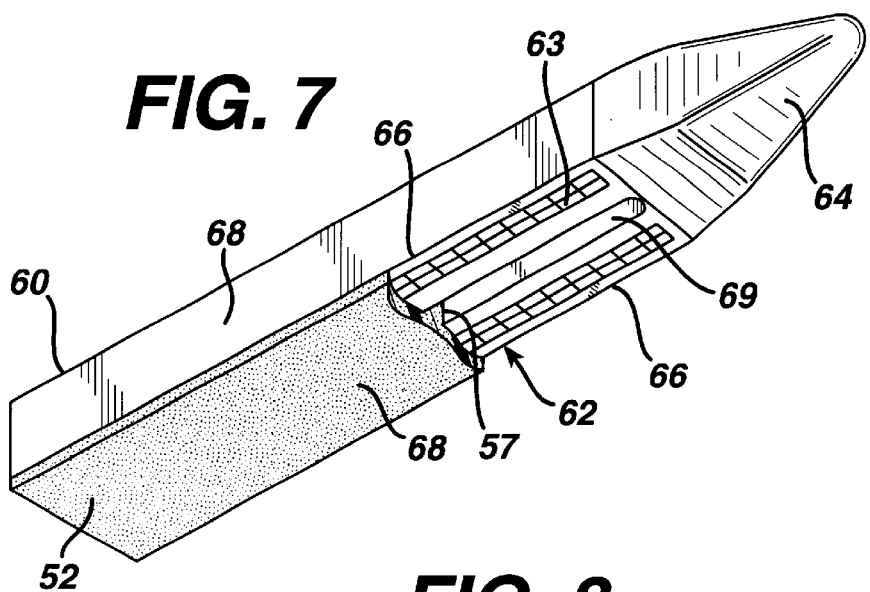
FIG. 7 is a perspective view of an anvil that includes a buttress in accordance with the present invention.
Figure 8:
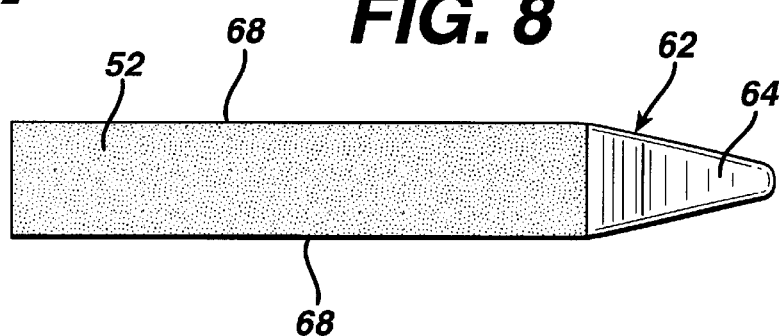
FIG. 8 is a top plan view of the anvil shown in FIG. 7.
Figure 9:
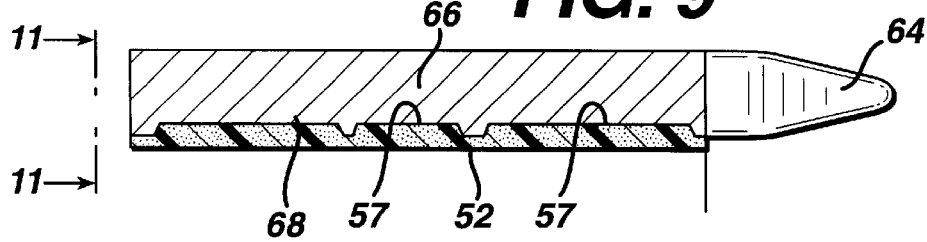
FIG. 9 is a side elevational view of the anvil shown in FIG. 7.
Figure 10:
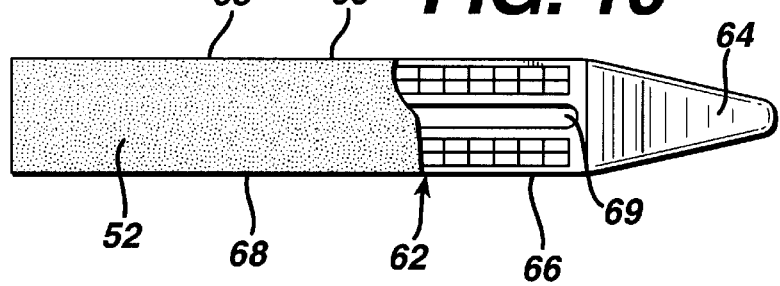
FIG. 10 is a bottom plan view of the anvil shown in FIG. 7.
Figure 11:
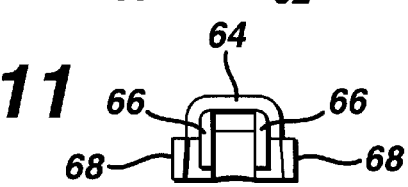
FIG. 11 is an end view of the anvil taken along line 11—11 in FIG. 9.

As shown in FIGS. 5 and 6, staples 51 extend through the buttress 52 and the tissue segments 70 and 72 sandwiched there between. The buttress 52 uniformly distributes pressure along the line of staples and thereby causes substantial hemostasis along the tissue cut and pneumostasis around the staple legs. The absorbable nature of the material from which the buttress are made allows the buttress to be left in the body and eliminates the potential for foreign body reactions that might occur if the buttress were not bioabsorbable.

In accordance with the most preferred embodiment of the invention, the foam material is positioned adjacent the surfaces of the tissue sections that contact both the staple cartridge 50 and the anvil tip 62. However, the invention contemplates that the buttress may be positioned adjacent only one of such surfaces, preferably the surface adjacent the anvil tip 62. Further, it is preferred that a pair of parallel lines of staples extend through each tissue section adjacent the tissue cut.

Although disclosed above in conjunction with a particular surgical stapler 10 for exemplary purposes, it is contemplated that the principles of the present invention may be similarly utilized in conjunction with other types of surgical staplers and cutters. For example, a circular stapler of the type disclosed in U.S. Pat. No. 5,104,025 may be suitably modified to provide buttresses on the staple cartridge and the anvil.

The invention in its broadest aspects is not limited to the specific details shown and described, and modifications may be made to the disclosed; preferred embodiments of the invention without departing from the principles of the invention.

EXAMPLES

Lyophilization Process for Producing Caprolactone Glycolide Foam Buttress with Attachment Projections An appropriate amount (16.5 gm) of polymer (nominal 40/60 CAP/GLY made in a manner similar to the methods described in U.S. Pat. No. 5,468,253) was placed in 1,4-dioxane solvent (148 ml) and stirred at about 50° C. for about 5 hours until dissolved to make a 10 weight percent solution. The solution was filtered cool through an extra course porosity filter (Kimble, Kimax Buchner funnel with Kimflow fritted disc, 150 ml capacity, extra course porosity—or equivalent) to remove undissolved polymer.

A mold was constructed of stainless steel, aluminum or other suitable mold material. A continuous pocket, or channel, or a plurality of longitudinally spaced pockets, or channels, are machined into the surface of the mold. The pockets, or channels, in the mold correspond to the knife guide channel in the anvil and/or staple cartridge which guides the knife blade in the staple cartridge and/or anvil used in the stapling apparatus. The number, dimension and spacial relationship of the pockets, or channels, are determined so as to provide a molded buttress which in turn provides a releasable pressure fit with knife guide channels of the anvil or staple cartridge when place in cooperation therewith.

An appropriate amount of the 10% solution (31.0 g for about a 0.030" thick) was placed in the mold. The mold containing the solution was placed on the shelf of the pre-cooled lyophilizer maintained at 20° C. The solution was then allowed to freeze to −5° C. by setting the shelf temperature to −5° C.

After 30 minutes, a vacuum was pulled. Two hours of primary drying at −5° C. under vacuum was required to remove most of the 1,4-dioxane. Upon conclusion of the initial drying phase, typically the vacuum level reaches about 10 mTorr or less. The second phase of drying was conducted in two stages under a 10 mTorr vacuum. First the shelf temperature was raised to 5° C. and held for 1 hour. The temperature then was raised to 20° C. and held for an additional 1 hour.

Upon conclusion of the second drying phase, the chamber was taken to room temperature and the vacuum was broken with nitrogen. The foams were removed from the molds and placed in plastic bags and stored under nitrogen.

The total cycle time for lyophilization was approximately 4.5 hours. Foams made by this process were determined to have <0.2 ppm of residual dioxane by headspace analysis.

What is claimed is:

1. A surgical stapling apparatus for hemostasis or pneumostasis of tissue, comprising:
   a staple cartridge comprising a plurality of surgical staples provided in two spaced apart lines, the cartridge having an upper surface with an opening through which said staples may be ejected and a knife guide channel, an anvil having a surface with an opening through which said staples may be received and a knife guide channel; and a buttress that provides sealing for hemostasis and pneumostasis, which buttress comprises a continuous projection, or a plurality of projections, wherein the projection(s) are of sufficient number, dimension and spacial relationship to provide a releasable pressure fit with means for receiving the projection(s) when placed in cooperation therewith, said means for receiving said projection being located on the staple cartridge or the anvil.

2. The apparatus of claim 1 wherein the buttress comprises a material selected from the group consisting of a bioabsorbable non-woven fabric and a bioabsorbable foam.

3. The apparatus of claim 2 wherein the bioabsorbable foam comprises an elastomeric aliphatic polyester.

4. The apparatus of claim 3 wherein the elastomeric aliphatic polyester is selected from the group consisting of a copolymer of ε-caprolactone and glycolide, a copolymer of ε-caprolactone and lactide, a copolymer of p-dioxanone and lactide, a copolymer of ε-caprolactone and p-dioxanone, a copolymer of p-dioxanone and trimethylene carbonate, a copolymer of trimethylene carbonate and glycolide and a copolymer of trimethylene carbonate and lactide.

5. The apparatus of claim 4 wherein the bioabsorbable foam comprises copolymers of ε-caprolactone and glycolide.

6. The apparatus of claim 1 wherein the projection(s) are located longitudinally along the mid-portion of the buttress and the means for receiving the projection(s) comprises the knife guide channel.

7. The apparatus of claim 3 wherein the buttress and the projection(s) comprise different elastomeric aliphatic polyesters.

8. A buttress for use in a surgical stapling apparatus that comprises a staple cartridge containing a plurality of surgical staples provided in two spaced apart lines, the cartridge having an upper surface with an opening through which said staples may be ejected and a knife guide channel, and an anvil comprising a surface with an opening through which said staples may be received and a knife guide channel, wherein the buttress comprises a continuous projection, or a plurality of projections, wherein the projection(s) are of sufficient number, dimension and spacial relationship to provide a releasable pressure fit with means for receiving the projection(s) of the staple cartridge or the anvil when placed in cooperation therewith.

9. The buttress of claim 8 comprising a material selected from the group consisting of a bioabsorbable non-woven fabric and a bioabsorbable foam.

10. The buttress of claim 9 wherein the bioabsorbable foam comprises an elastomeric aliphatic polyester.

11. The buttress of claim 10 wherein the elastomeric aliphatic polyester is selected from the group consisting of a copolymer of ε-caprolactone and glycolide, a copolymer of ε-caprolactone and lactide, a copolymer of p-dioxanone and lactide, a copolymer of ε-caprolactone and p-dioxanone, a copolymer of p-dioxanone and trimethylene carbonate, a copolymer of trimethylene carbonate and glycolide and a copolymer of trimethylene carbonate and lactide.

12. The buttress of claim 8 wherein the bioabsorbable foam comprises copolymers of ε-caprolactone and glycolide.

13. The buttress of claim 8 wherein the projection(s) are located longitudinally along the mid-portion of the buttress and the means for receiving the projection(s) comprises the knife guide channel.

14. The buttress of claim 10 wherein the buttress and the projection(s) comprise different elastomeric aliphatic polyesters.

* * * * *